(12) United States Patent
Arndts et al.

(10) Patent No.: US 6,476,047 B2
(45) Date of Patent: Nov. 5, 2002

(54) ANELLATED DIHYDROPYRIDINES FOR THE TREATMENT OF CHRONIC PAIN

(75) Inventors: Dietrich Arndts, Appenheim (DE); Walter Loesel, Mainz (DE); Wolfram Gaida, Ingelheim (DE); Klaus Klinder, Ingelheim (DE); Stefan Matthias Blech, Warthausen (DE); Henning Draheim, Ingelheim (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/908,962

(22) Filed: Jul. 19, 2001

(65) Prior Publication Data

US 2002/0045640 A1 Apr. 18, 2002

Related U.S. Application Data

(60) Provisional application No. 60/223,871, filed on Aug. 8, 2000.

(30) Foreign Application Priority Data

Jul. 25, 2000 (DE) ......................... 100 35 997

(51) Int. Cl.⁷ ................. C07D 217/16; A61K 31/47
(52) U.S. Cl. ....................... 514/307; 546/139
(58) Field of Search ................ 546/139; 514/307

(56) References Cited

FOREIGN PATENT DOCUMENTS

| | | |
|---|---|---|
| EP | 0 491 441 | 6/1992 |
| GB | 2 236 674 | 4/1991 |

OTHER PUBLICATIONS

Dray, A. et al; "Pharmacology of chronic pain"; Trends in Pharmacological Sciences 1994; 15, 190–197.

Primary Examiner—Zinna Northington Davis
(74) Attorney, Agent, or Firm—Robert P. Raymond; Philip I. Datlow; Alan R. Stempel

(57) ABSTRACT

The invention relates to the use of anellated dihydropyridines according to the following formula I, and the salts thereof with physiologically acceptable acids, for the treatment of chronic pain, wherein A is benzo or thieno and Z, $R^1$, $R^2$, $R^3$, $R^4$, $R^5$ and $R^6$ are defined as in the specification:

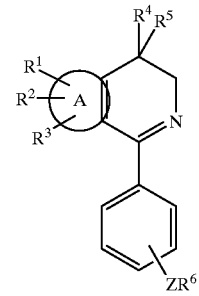

I

The inventions also relates to novel compounds of formula I and pharmaceutical compositions thereof.

9 Claims, No Drawings

ANELLATED DIHYDROPYRIDINES FOR THE TREATMENT OF CHRONIC PAIN

CROSS-REFERENCE TO RELATED APPLICATIONS

Benefit of U.S. Provisional Application Serial No. 60/223,871, filed on Aug. 8, 2000 is hereby claimed, and that application is incorporated herein by reference in its entirety.

FIELD OF THE INVENTION

The invention relates to the use of anellated dihydropyridines and the salts thereof with physiologically acceptable acids for preparing agents for the treatment of chronic pain.

BACKGROUND OF THE INVENTION

EP 0 491 441 A1, describes the compound of Formula

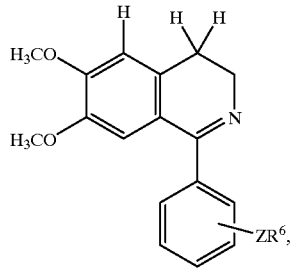

wherein $ZR^6$ denotes para-phenoxy. There is no reference therein to the treatment of chronic pain.

British Patent 2236674 describes compounds for treating pain and/or CNS-diseases in which $R^4$ and $R^5$ denote hydrogen, Z denotes a bond and $R^6$ denotes a $C_1$–$C_5$ alkyl, aryl or aryl-lower alkyl group. These compounds act as GABA antagonists on GABA-autoreceptors.

Diseases connected with chronic or chronically recurring pain include, inter alia, migraine, neuralgia, muscle pain and inflammatory pain. They have mechanisms in common with chronically recurring pain [Dray, A. Urban L. and Dickenson, A. Trends in Pharmacological Sciences 1994; 15:190–197].

The chronic neuronal pains include inter alia postoperative pain, shingles, phantom pain, diabetic neuropathy, pain after chronic nerve compression as well as AIDS and cancer in their final stages.

The aim of the present invention is to provide an active substance for treating chronic pain, particularly chronic neuronal pain, with good bioavailability and a powerful antinociceptive activity.

BRIEF SUMMARY OF THE INVENTION

In one general aspect, the present invention is directed to a method of treating chronic pain by the administration of a compound of formula I or a pharmaceutically acceptable salt thereof:

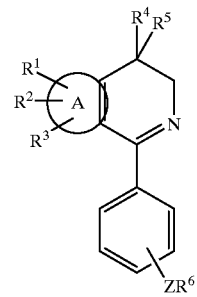

wherein A is benzo or thieno,
and if A is benzo
$R^1$, $R^2$ and $R^3$ independently of one another denote
H, OH, $C_1$–$C_5$ alkyl, $C_1$–$C_5$ alkoxy, —O—$(CH_2)_{1\text{-}5}$—$OCH_3$
or $R^2$ and $R^3$ together form the group
—O—$CH_2$—O—, and
if A is thieno, $R^1$, $R^2$ and $R^3$ denote hydrogen;
$R^4$ and $R^5$ independently of one another denote
H, $C_1$–$C_5$ alkyl or
Together with the central atom to which they are bonded form a $C_3$–$C_7$ ring.
$R^6$ denotes $C_1$–$C_{12}$ alkyl or a phenyl or benzyl group substituted by the groups $R^7$ and $R^8$,
wherein $R^7$ and $R^8$ independently of one another denote hydrogen, halogen (F, Cl, Br, I), $C_1$–$C_5$ alkyl, $C_1$–$C_5$ alkoxy or $C_1$–$C_5$ fluoroalkyl group.
Z denotes O, S or an NHCO— group or, if at least one of the groups $R^4$ and $R^5$ is other than hydrogen, Z may also denote a single bond.

In a second general aspect, the present invention is directed to a compound of formula I above, or a pharmaceutically acceptable salt thereof, with the proviso that the compound of the following formula:

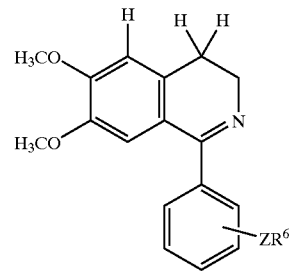

wherein $ZR^6$=para-phenoxy is excluded. The present invention is also directed to pharmaceutical compositions comprising these compounds of formula I or a pharmaceutically acceptable salt thereof.

DETAILED DESCRIPTION OF THE INVENTION

Surprisingly, the compounds according to the present invention exhibit a powerful antinociceptive activity based on the blockade of voltage-dependent N-type $Ca^{+2}$-channels.

The invention therefore relates to the use of the compounds of Formula I, or the salts thereof with physiologically acceptable acids, for the preparation of a pharmaceutical composition for treating chronic pain:

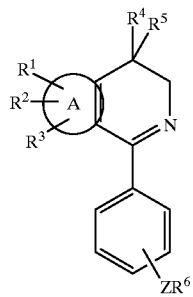

I wherein A is benzo or thieno, and if A is benzo $R^1$, $R^2$ and $R^3$ independently of one another denote H, OH, $C_1$–$C_5$ alkyl, $C_1$–$C_5$ alkoxy, —O—$(CH_2)_{1-5}$—$OCH_3$ or $R^2$ and $R^3$ in positions 6 and 7 together form the group —O—$CH_2$—O—, and if A is thieno, $R^1$, $R_2$ and $R^3$ denote hydrogen;

$R^4$ and $R^5$ independently of one another denote

H, $C_1$–$C_5$ alkyl or together with the central atom to which they are bonded form a $C_3$–$C_7$ ring.

$R^6$ denotes $C_1$–$C_{12}$ alkyl or a phenyl or benzyl group substituted by the groups $R^7$ and $R^8$, wherein $R^7$ and $R^8$ independently of one another denote hydrogen, halogen (F, Cl, Br, I), $C_1$–$C_5$ alkyl, $C_1$–$C_5$ alkoxy or $C_1$–$C_5$ fluoroalkyl group.

Z denotes O, S or an NHCO— group or, if at least one of the groups $R^4$ and $R^5$ is other than hydrogen, Z may also denote a single bond.

The invention further relates to the compounds of Formula I above, with the proviso that the compound of the following formula:

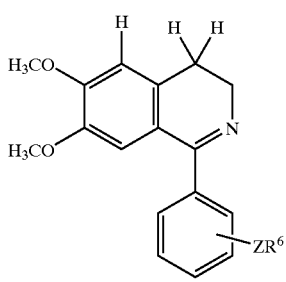

wherein $ZR^6$=para-phenoxy is excluded.

Preferred compounds are the compounds of Formula IA and their use as described above,

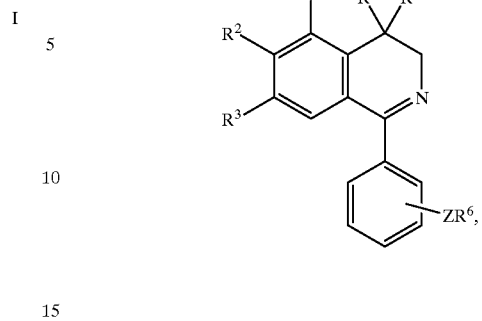

IA wherein $R^1$, $R^2$ and $R^3$ preferably independently of one another denote hydrogen, methyl or methoxy, particularly wherein $R^2$ and $R^3$ denote methoxy and $R^1$ is methoxy or hydrogen.

Also preferred are compounds of general Formula I and their use as specified above wherein $R^4$ and $R^5$ independently of each other denote hydrogen or a methyl group.

Particularly preferred are compounds of general Formula I and their use as described above, wherein Z—$R^6$ denotes a group of general Formula II, III or IV:

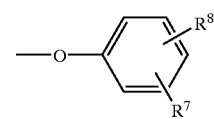

II

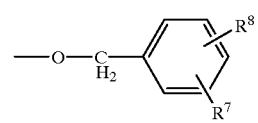

III

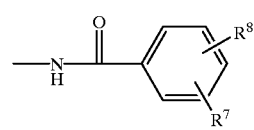

IV

Particularly preferred are compounds of general Formula I and their use as described above wherein $R^6$ denotes $C_6$–$C_{10}$ alkyl.

Additional embodiments are compounds of general Formula I and their use as described above, wherein Z—$R^6$ denotes a phenoxy group of formula II in the ortho or para-position;

Additional embodiments are compounds of general Formula I and their use as described above, wherein at least one of the groups $R^7$ and $R^8$ denotes a $CF_3$ group or an F atom.

Additional embodiments are compounds of general Formula I and their use as described above, wherein the compound of formula I is a compound of the following formula:

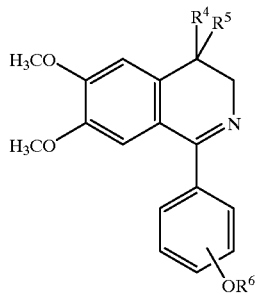

wherein R⁴ and R⁵ simultaneously denote hydrogen or methyl, and R⁶ denotes a group of formula V, VI or VII:

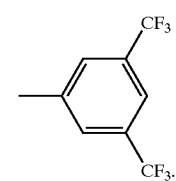  V

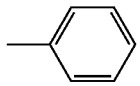  VI

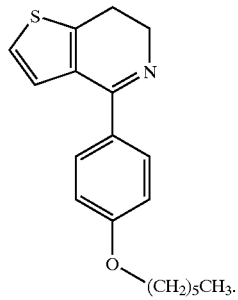  VII

Additional embodiments are compounds of general Formula I and their use as described above, wherein the compound of formula I is a compound of the following formula:

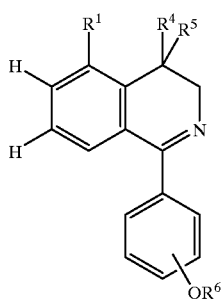

wherein R¹ denotes methyl or methoxy, R⁴ and R⁵ simultaneously denote hydrogen or methyl, and R⁶ denotes a group of formula V or VII:

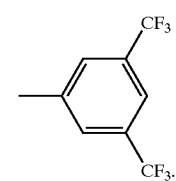  V

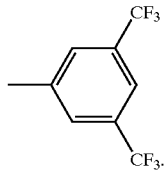  VII

An additional embodiment is compounds of general Formula I and their use as described above, wherein the compound of formula I is a compound of the following formula:

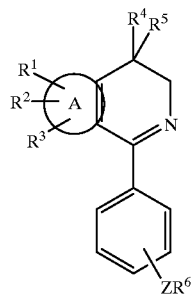

Another general aspect of the invention is directed to a compound of the following formula I, or a pharmaceutically acceptable salt thereof:

I wherein A is benzo or thieno,
and if A is benzo
R¹, R² and R³ independently of one another denote H, OH, C₁–C₅ alkyl, C₁–C₅ alkoxy, —O—(CH₂)₁₋₅—OCH₃,
or R² and R³ together form the group
—O—CH₂—O—, and
if A is thieno, R¹, R² and R³ denote hydrogen;
R⁴ and R⁵ independently of one another denote
H, C₁–C₅ alkyl or together with the atom to which they are bonded form a C₃–C₇ ring;
R⁶ denotes C₁–C₁₂ alkyl, or denotes a phenyl or benzyl group each substituted by the groups R⁷ and R⁸,
wherein R⁷ and R⁸ independently of one another denote hydrogen, halogen, C₁–C₅ alkyl, C₁–C₅ alkoxy or C₁–C₅ fluoroalkyl group;
Z denotes O, S or an NHCO— group or, if at least one of the groups R⁴ and R⁵ is other than hydrogen, Z may also denote a single bond.
with the proviso that the compound of the following formula is excluded:

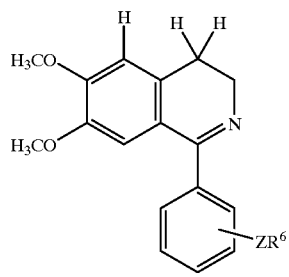

wherein $ZR^6$=para-phenoxy.

One embodiment is directed to a compound of formula I above, or a pharmaceutically acceptable salt thereof, wherein $Z-R^6$ denotes a group of formula II or IV:

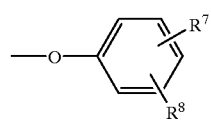

II

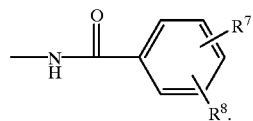

IV

Another embodiment is directed to a compound of formula I above, wherein $R^4$ and $R^5$ simultaneously denote hydrogen or methyl, and $R^6$ denotes a group of formula V, VI or VII:

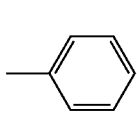

V

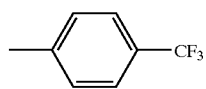

VI

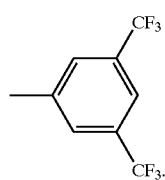

VII

Another embodiment is directed to a compound of formula I above, wherein the compound has the following formula:

wherein R methyl or methoxy, $R^4$ and $R^5$ simultaneously denote hydrogen or methyl and $R^6$ denotes a group of formula V or VII:

V

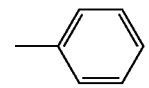

VII

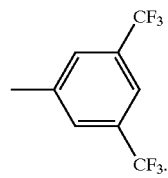

Another embodiment is directed to a pharmaceutical composition comprising a compound of formula I described above.

Acids suitable for forming the salts of the compounds according to the invention include, for example, hydrochloric acid hydrobromic acid, sulphuric acid, phosphoric acid, nitric acid, oxalic acid, malonic acid, fumaric acid, maleic acid, tartaric acid, citric acid, ascorbic acid and methanesulphonic acid.

The term alkyl groups denotes branched and unbranched alkyl groups having 1 to 12, preferably 2 to 10, most preferably 5 to 6 carbon atoms, including, for example: methyl, ethyl, n-propyl, iso-propyl, n-butyl, iso-butyl, sec. butyl, tert.-butyl, n-pentyl, iso-pentyl, neo-pentyl and n-hexyl, but also n-decyl.

The term alkoxy groups denotes branched and unbranched alkoxy groups having 1 to 5 carbon atoms, including for example: methyloxy, ethyloxy, n-propyloxy, iso-propyloxy, n-butyloxy, iso-butyloxy, sec. butyloxy, tert.-butyloxy, n-pentyloxy, iso-pentyloxy and neo-pentyloxy.

The term cycloalkyl groups having 3 to 7 carbon atom denotes cyclopropyl, cyclobutyl, cyclopentyl, cyclohexyl or cycloheptyl.

The term fluoroalkyl groups denotes branched and unbranched fluoroalkyl groups having 1 to 5 carbon atoms and 1 to the maximum possible number of fluorine atoms, preferably 1,1,1-trifluoroethyl, most preferably trifluoromethyl.

The compounds according to the invention are intended to be illustrated by the Examples which follow. The skilled person will be aware that the Examples are intended solely as an illustration and not to be regarded as limiting.

EXAMPLES

TABLE 1

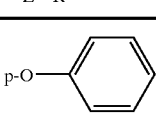

| No. | R¹ | R² | R³ | R⁴ | R⁵ | —Z—R⁶ | Salt form | Mp(° C.) |
|---|---|---|---|---|---|---|---|---|
| 1 | H | OCH₃ | OCH₃ | H | H | p-O—C₆H₅ | Cl | 209–210 |
| 2 | H | OCH₃ | OCH₃ | H | H | p-O—(C₆H₁₃)ₙ | Cl | 172 |
| 3 | OCH₃ | OCH₃ | OCH₃ | H | H | p-O—C₆H₅ | Cl | 173–175 |
| 4 | H | OCH₃ | OCH₃ | CH₃ | CH₃ | p-O—C₆H₅ | Free Base | 141–142 |
| 5 | H | OCH₃ | OCH₃ | CH₃ | CH₃ | p-O—C₆H₄—CF₃ | Cl | 195–198 |
| 6 | H | OCH₃ | OCH₃ | H | H | p-O—C₆H₄—CF₃ | Cl | 218 |
| 7 | H | OCH₃ | OCH₃ | CH₃ | CH₃ | p-O—C₆H₃(CF₃)₂ | Cl | 197 |
| 8 | H | OCH₃ | OCH₃ | CH₃ | CH₃ | o-O—C₆H₃(CF₃)₂ | Cl | 172–173 |
| 9 | H | H | H | CH₃ | CH₃ | o-O—C₆H₃(CF₃)₂ | Cl | 211–212 |

TABLE 1-continued
| No. | R¹ | R² | R³ | R⁴ | R⁵ | —Z—R⁶ | Salt form | Mp(° C.) |
|---|---|---|---|---|---|---|---|---|
| 10 | H | OCH$_3$ | OCH$_3$ | H | H | 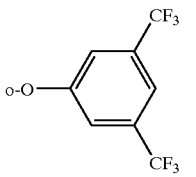 | Cl | 215 |
| 11 | H | H | H | CH$_3$ | CH$_3$ | P—O—(C$_6$H$_{13}$)$_n$ | Cl | 186–187 |
| 12 | H | OCH$_3$ | H | CH$_3$ | CH$_3$ | 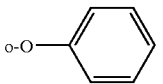 | Cl | 122–123 |
| 13 | OCH$_3$ | H | H | H | H | 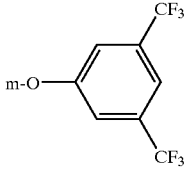 | Cl | 162–166 |
| 14 | H | OCH$_3$ | OCH$_3$ | CH$_3$ | CH$_3$ | 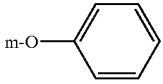 | Cl | 210–211 |
| 15 | H | OCH$_3$ | OCH$_3$ | CH$_3$ | CH$_3$ | 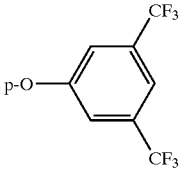 | Cl | 181 |
| 16 | H | H | H | CH$_3$ | CH$_3$ | 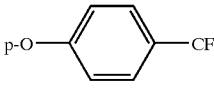 | Cl | 217–218 |
| 17 | H | H | H | H | H |  | Cl | 234–235 | p: para position
m: meta position
o: ortho position

Example 18

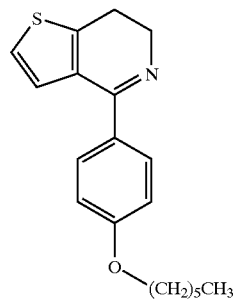

Assessment of Biological Activity

The compounds according to this invention exhibit an antinociceptive activity which is based on the blockade of voltage-dependent N-type $Ca^{+2}$-channels.

The blocking action on voltage-dependent N-type calcium channels was demonstrated on primary cell cultures of FLUO-3 charged recombinant HEK-cells expressing N-type $Ca^{+2}$-channels, by fluorescent recording to the cytosolic calcium kinetics after potassium depolarisation (80 mM $K^+$) (Test A). The concentration of the half-maximum inhibition ($IC_{50}$-values) for the selected substances is in the submicro- to micromolar range. Independently of this optical method of measurement, the inhibitory effect on the N-type calcium channels was confirmed independently, by an electrophysiological method, using the patch-clamp technique on the same type of cells (Test B). Table 2 shows the pharmacological in vitro data obtained for selected compounds.

TABLE 2

Test A: Calcium Imaging
Inhibition of N-type calcium channels in HEK-293 cell
Test B: Patch-clamp Tests
N-type calcium channel blockade in HEK-293-N26 cells

| Example No. | $IC_{50}$-values ($10^{-6}$M) | |
|---|---|---|
| | Test A | Test B |
| 1 | 1.86 | 1.80 |
| 2 | 1.20 | 1.09 |
| 3 | 1.94 | |
| 4 | 1.83 | |
| 5 | 0.82 | 1.33 |
| 6 | 0.94 | 1.12 |
| 7 | 1.26 | 1.00 |
| 8 | 3.16 | 1.70 |
| 9 | 3.98 | 0.26 |
| 10 | 1.95 | |
| 11 | 3.26 | |
| 12 | 5.54 | 1.60 |
| 14 | 1.61 | |
| 15 | 1.62 | |
| 16 | | 1.22 |
| 17 | | 8.20 |

Proof of the analgesic activity of the channel blockade in animal experiments was achieved by the formalin paw test and the CCI Bennett model on two independent pain models in rats. The tests are described below. The test results are shown in Table 3.

Formalin Paw Test (Test C)

Male rats (Chbb: THOM) weighing 250–300 grams are used. 20 µl of a 2% formaldehyde solution is injected into the plantar region of the right hind paw. Immediately afterwards, the number of flinches (spasms of the affected hind paw) and the time spent licking the affected paw are recorded. After 5 minutes in each case the values are collated into epochs. Time-activity curves for flinches and licking are plotted from the epoch values. Typically, two phases of the formalin activity (flinches, licking) are observed. A first phase of 0–10 minutes and a second phase of 10–60 minutes. Between the two phases the number of flinches and the duration of licking fall towards 0 (interphase). The areas under the curve for the first phase and for the second phase are determined from the timeactivity curves. Usually 5 animals are used in each case for the control, placebo and dose of active substance. The results of the doses of active substance are compared with those of the control and $ED_{50}$ values are calculated. $ED_{50}$ is the dose at which the control values are inhibited by 50%.

Chronic Constriction Injury (CCI, Bennett Model) (Test D)

The principle of the method is producing hyperalgesia and allodynia in the plantar region (the sole of the hind paw). Sprague-Dawley rats (Harlan) weighing 250–350 grams are used.

Under anaesthetic, four loose ligatures are placed on the sciatic nerve of the left hind paw at intervals of 2.5 mm in such a way that the perinerval circulation is affected but not prevented. This leads to extravasation and oedema, resulting in neuropathy of the nerves which innervate the planter region. The right hind paw is treated in the same way without the ligatures. Control tests for allodynia and/or hyperalgesia are carried out without the administration of any substance before and 8–10 days after the operation. Then substance tests are carried out at intervals of 2–3 days. The effects of the substance on the various parameters and $ED_{50}$ values are calculated (=doses which inhibit by 50% the allodynic or hyperalgesic effects of the stimulation).

Heat Hyperalgesia (Plantar-test)

The animals are placed on a glass platform through which an increasingly powerful heat producing radiant source is directed onto the sole of the hind paws (Plantar-test). The length of time between the start of the radiation and the reaction of lifting the foot away is recorded by means of a photoelectric cell. The paw which has been operated on and the control paw are compared.

Mechano-hyperalgesia (Pin Prick)

The animals are placed in cages with a wire mesh base. Using a blunt needle (e.g. a large safety pin) the skin of the sole of the paw (Plantar-region) is touched so that an indentation is only just produced. Similarly, the sole of the paw is pinched gently with forceps. Normal animals react to this stimulus only slightly or not at all. Animals with CCI withdraw their paws very much more quickly (away from the pin) and hold them in the air for longer (holding away). The number and duration of positive reactions of the operated and control paws are measured.

Mechano-Allodynia (von Frey Hairs)

The animals are put in cages with a wire mesh base. The skin (Plantar-region) of the hind paw is touched with fibres of varying flexibility (von Frey hairs) until the fibre bends. The tester examines which thickness of fibre causes the animals to raise their operated or control paws.

Cold-allodynia (Acetone Evaporation Coldness)

The animals are placed in cages with a wire mesh base. Using a small spray, acetone is carefully applied to the sole of the hind paw (Plantar-region) from below. The healthy animals reacts to this cold stimulus only slightly by raising the paw. Animals with CCI react more frequently and distinctly with their affected paw. The latency period until the operated or control paw is raised and the duration are observed and measured over an observation period of 5 minutes.

TABLE 3

Test C: Formalin-paw Test (Rat)

Inhibition of flinching ($ED_{50}$ values in mg/kg; p.o.)

Test D: Benett (CCI)-Model (Rat)

Measuring parameter: mechanohyperalgesia ($ED_{50}$ values in mg/kg; p.o.)

| Example | $ED_{50}$ values in mg/kg; p.o. | |
|---|---|---|
| No. | Test C | Test D |
| 1 | 10 | |
| 5 | 15 | 10 |
| 9 | 10 | |

The compounds may be administered both enterally and parenterally. A proposed dose for oral administration is 0.1 to 500 mg of active of active substance per dose, whilst for intravenous administration a dose of 0.05 to 150 mg per dose is suggested. The desired therapeutic dose depends on the preparation and can be determined experimentally.

Examples of Pharmaceutical Formulations a) Coated tablets 1 tablet core contains:

| | |
|---|---|
| Active substance of general formula I | 30.0 mg |
| Lactose | 100.0 mg |
| Maize starch | 75.0 mg |
| Gelatine | 3.0 mg |
| Magnesium stearate | 2.0 mg |
| | 210.0 mg |

Preparation:

The mixture of the active substance with lactose and maize starch is granulated with a 10% aqueous gelatine solution through a screen with a 1 mm mesh, dried at 40° C. and passed through a screen again. The granules thus obtained are mixed with magnesium stearate and compressed. The resulting cores are coated in the usual way with a coating applied using an aqueous suspension of sugar, titanium dioxide, talc and gum arabic. The finished coated tablets are polished with beeswax.

b) Tablets

| | |
|---|---|
| Active substance of general formula I | 30.0 mg |
| Lactose | 100.0 mg |
| Maize starch | 70.0 mg |
| Soluble starch | 7.0 mg |
| Magnesium stearate | 3.0 mg |
| | 210.0 mg |

Preparation:

The active substance and magnesium stearate are granulated with an aqueous solution of the soluble starch, the granules are dried and intimately mixed with lactose and maize starch. The mixture is then compressed to form tablets weighing 210 mg.

c) Capsules

| | |
|---|---|
| Active substance according to claim 1 | 20.0 mg |
| Lactose | 230.0 mg |
| Maize starch | 40.0 mg |
| Talc | 10.0 mg |
| | 300.0 mg |

Preparation:

The active substance, lactose and maize starch are first combined in a mixer and then in a grinder. The mixture is returned to the grinder, thoroughly mixed with the talc and mechanically packed into hard gelatine capsules.

PREPARATION EXAMPLES

The compounds of general formula (I) may be prepared by methods known per se as illustrated in the following Examples.

I. Preparation of 3,4-dihydro-6,7-dimethoxy-1-(4-phenoxyphenyl)isoquinoline

1. Preparation of N-(2-(3,4-dimethoxyphenyl)ethyl)-4-phenoxybenzoic acid amide.

2.5 g (12 mmol) of 4-phenoxybenzoic acid are reacted with 2.0 g (12.5 mmol) of N, N'-carbonyldiimidazole, at ambient temperature, with stirring, in 50 ml of anhydrous methylene chloride. After about 30 min. 2.35 g of 2-(3,4-dimethoxyphenyl)ethylamine are added. When the reaction has ended the reaction mixture is extracted successively with 2 N HCl, water and saturated NaCl solution. The organic phase is dried over $Na_2SO_4$ and the solvent is evaporated off. The crystalline residue is used without further purification for the subsequent cyclisation.

2. Preparation of 3,4-dihydro-6,7-dimethoxy-1-(4-phenoxy-phenyl)isoquinoline-methanesulphonate.

5.0 g (14 mmol) of N-(2-(3,4-dimethoxyphenyl)ethyl-4-phenoxy-benzoic acid amide are refluxed for 1 hour in a mixture of 20 ml of acetonitrile and 4 ml of phosphorus oxychloride. After the reaction has ended (monitored by TLC) the reaction medium is evaporated off in vacuo. The residue is dissolved in water, made alkaline by the addition of 2N NaOH, then extracted several times using $CH_2Cl_2$. The combined organic phases are washed with water and dried over $Na_2SO_4$. After evaporation of the solvent the residue is taken up in ethanol, filtered through activated charcoal and crystallised by the addition of methanesulphonic acid. Mp 175° C.

II Preparation of 3,4-dihydro-4,4-dimethyl-1-[2-(3,5-ditrifluoromethyl)phenoxy]phenyl-isoquinoline hydrochloride A mixture of 6.8 g of N-[2-(2,2-dimethylphenyl)ethyl]-2-[(3,5-ditrifluoromethyl)phenoxy]-benzamide, 10 ml of $POCl_3$ and 80 ml of acetonitrile was refluxed for 2 hours. When the reaction had ended (monitored by TLC) the reaction mixture was added dropwise to an ice-cold soda solution. The reaction product was extracted with $CH_2Cl_2$. The combined organic phases were washed with water, dried over $Na_2SO_4$ and evaporated in vacuo. The crude product was taken up in acetone, converted into the hydrochloride by the addition of ethereal HCl and crystallised by the careful addition of ether (white crystals).

Mp.: 211–212° C.

All the other compounds in this invention can be prepared analogously to this method described above.

We claim:

1. A compound of the following formula I, or a pharmaceutically acceptable salt thereof:

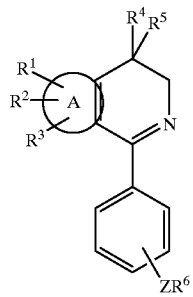

I wherein A is benzo, $R^1$, $R^2$ and $R^3$ independently of one another denote H, OH, $C_1$–$C_5$ alkyl, $C_1$–$C_5$ alkoxy, or —O—$(CH_2)_{1-5}$—$OCH_3$, or $R^2$ and $R^3$ together form the group —O—$CH_2$—O—, $R^4$ and $R^5$ independently of one another denote H, or $C_1$–$C_5$ alkyl or together with the atom to which they are bonded form a $C_3$–$C_7$ ring;

$R^6$ denotes $C_1$–$C_{12}$ alkyl, or denotes a phenyl or benzyl group each substituted by the groups $R^7$ and $R^8$, wherein $R^7$ and $R^8$ independently of one another denote hydrogen, halogen, $C_1$–$C_5$ alkyl, $C_1$–$C_5$ alkoxy or $C_1$–$C_5$ fluoroalkyl group;

Z denotes O, S or an NHCO— group or, if at least one of the groups $R^4$ and $R^5$ is other than hydrogen, Z may also denote a single bond;

with the proviso that when Z is O or S, then $R^6$ cannot be $C_1$–$C_{12}$ alkyl, or phenyl substituted by the groups $R^6$ and $R^8$, wherein $R^7$ and $R^8$ independently of one another denote hydrogen or halogen.

2. A compound of formula I according to claim 1, or a pharmaceutically acceptable salt thereof, wherein Z—$R^6$ denotes a group of formula II or IV:

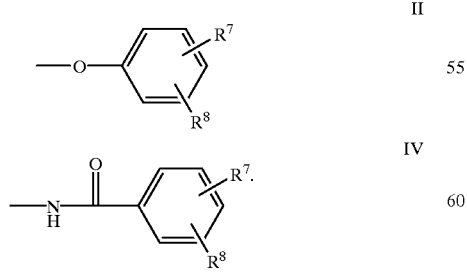

3. A compound of formula I according to claim 1 wherein $R^4$ and $R^5$ simultaneously denote hydrogen or methyl, and $R^6$ denotes a group of formula V, VI or VII:

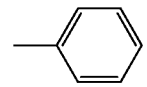

V

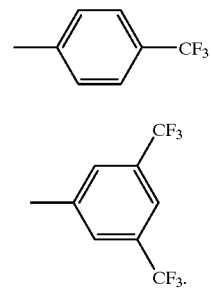

VI

VII

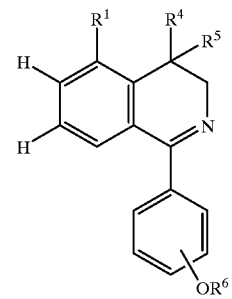

4. A compound of formula I according to claim 1 having the following formula:

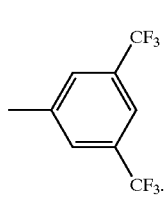

wherein $R^1$ methyl or methoxy, $R^4$ and $R^5$ simultaneously denote hydrogen or methyl and $R^6$ denotes a group of formula VII:

VII

5. A pharmaceutical composition comprising a compound according to any one of claims 1 to 4.

6. A compound of the following formula 1, or a pharmaceutially acceptable salt thereof:

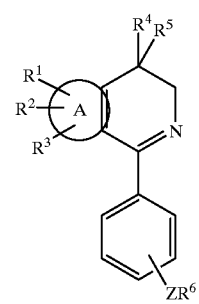

I wherein A is benzo;

$R^1$, $R^2$ and $R^3$ independently of one another denote H, OH, $C_1$–$C_5$ alkyl, $C_1$–$C_5$ alkoxy, or —O—$(CH_2)_{1-5}$—$OCH_3$, or $R^2$ and $R^3$ together form the group —O—$CH_2$—O—, and $R^4$ and $R^5$ independently of one another denote H, or $C_1$–$C_5$ alkyl or together with the atom to which they are bonded form a $C_3$–$C_7$ ring;

$R^6$ denotes a phenyl or benzyl group each substituted by the groups $R^7$ and $R^8$, wherein $R^7$ and $R^8$ independently of one another denote $C_1$–$C_5$ alkyl, $C_1$–$C_5$ alkoxy or $C_1$–$C_5$ fluoroalkyl group;

Z denotes O, S or an NHCO— group or, if at least one of the groups $R^4$ and $R^5$ is other than hydrogen, Z may also denote a single bond.

7. A compound of formula I according to claim 6, or a pharmaceutically acceptable salt thereof, wherein Z-$R^6$ denotes a group of formula II or IV:

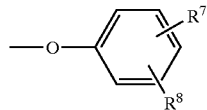

II

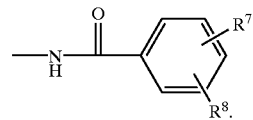

IV

8. A compound of formula I according to claim 6, wherein $R^4$ and $R^5$ simultaneously denote hydrogen or methyl, and $R^6$ denotes a group of formula VI or VII;

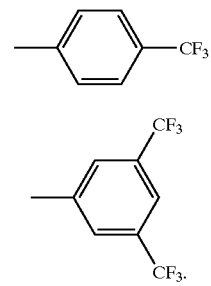

VI

VII

9. A pharmaceutical composition comprising a compound according to any one of claims 6 to 8.

* * * * *

UNITED STATES PATENT AND TRADEMARK OFFICE
CERTIFICATE OF CORRECTION

PATENT NO.      : 6,476,047 B2
DATED           : Novmber 5, 2002
INVENTOR(S)     : Dietrich Arndts et al.

It is certified that error appears in the above-identified patent and that said Letters Patent is hereby corrected as shown below:

<u>Column 17,</u>
Line 45, delete "groups $R^6$" and insert -- groups $R^7$ --

Signed and Sealed this

Eighteenth Day of February, 2003

JAMES E. ROGAN
*Director of the United States Patent and Trademark Office*